United States Patent [19]

Katz et al.

[11] Patent Number: 5,266,608
[45] Date of Patent: Nov. 30, 1993

[54] BIOMEDICAL ADHESIVE COMPOSITIONS

[75] Inventors: Dov Katz; Esther Brandeis, both of Haifa, Israel; Joachim Klein, Braunsdiweig, Fed. Rep. of Germany

[73] Assignees: Technion Research & Dev't Foundation, Ltd., Israel; GBF Gesellschaft fur Biotechnologische Forschung, Fed. Rep. of Germany

[21] Appl. No.: 722,088

[22] Filed: Jun. 27, 1991

[30] Foreign Application Priority Data

Jun. 29, 1990 [IL] Israel ...................... 094910

[51] Int. Cl.$^5$ ............................................. A61K 47/30
[52] U.S. Cl. ...................... 523/111; 523/113; 523/116; 523/118
[58] Field of Search .................. 527/118; 523/113, 14, 523/111, 16; 528/65, 55, 56, 57, 58; 424/449; 525/453; 524/788

[56] References Cited

U.S. PATENT DOCUMENTS

| | | | |
|---|---|---|---|
| 4,557,691 | 12/1985 | Martin et al. | 523/116 |
| 4,623,709 | 11/1986 | Bauriedel | 528/65 |
| 4,740,534 | 4/1988 | Matsuda et al. | 523/118 |
| 4,804,691 | 2/1989 | English et al. | 523/118 |
| 4,971,800 | 11/1990 | Chess et al. | 428/449 |
| 5,051,260 | 9/1991 | Chess et al. | 424/449 |
| 5,064,653 | 11/1991 | Sessions et al. | 424/445 |

FOREIGN PATENT DOCUMENTS 0332405 9/1989 European Pat. Off. .
1489163 10/1977 United Kingdom .

OTHER PUBLICATIONS

G. Meyer et al. *Biomat. Med. Dev. Art. Org.* (1979), 7(1), 55-71.
J. Kilpikari et al. *J. of Biomed Mat. Research* (1986), 20, 1095-1102.

Primary Examiner—Thurman K. Page
Assistant Examiner—P. Kulkosky
Attorney, Agent, or Firm—Morgan & Finnegan

[57] ABSTRACT

Novel non-elastomeric biomedical adhesive compositions for calcified tissues, are described. The compositions are characterized by a network structure which is obtained by the reaction of a polyisocyanate having at least two isocyanate groups with at least one polyol which possesses surface wetting properties with the participation of compounds selected from calcium and phosphorus, optional in the presence of a catalyst. The polyisocyanate is selected from aliphatic, alicyclic and aromatic compounds and preferred amounts are in the range of 20% to 80% by weight of the total amount of reactants. The polyol is selected from polyalkylene ether glycols and polyester glycols containing between 25 to 75 carbon atoms and preferred amounts are in the range of 10% to 80% by weight of the total amount of reactants. The adhesive compositions were found to produce a fast bonding of the calcified tissues, with a joint strength of above 0.5 N/sq.mm.

10 Claims, No Drawings

BIOMEDICAL ADHESIVE COMPOSITIONS

The present invention relates to adhesives compositions to be useful in biomedical applications. More particularly, the invention relates to new type of medical polymer adhesive compositions to be used in the treatment of bone fractures and for gluing of calcified body tissues.

BACKGROUND OF THE INVENTION

Various adhesive compositions were suggested in the last thirty years to replace the conventional metal assisted osteosynthesis method which uses various devices such as screws, plates and nails, in the treatment of fractures. Such compositions may offer a number of advantages over the conventional method such as bonding of particular fractures, ease and speed of fixation of fractures, excessive stiffness of current metal plates while providing a rigid fixation, etc.

Adhesive compositions to be useful for biomedical applications should respond to a quite large number of criteria such as:
to be inert;
to be non-toxic by itself or by its degradation products;
to be non-carcinogenic and non-allergenic at long and short term;
to be absorbed within the specific time of healing of the tissues that it binds;
to allow the adjacent tissues to grow and unite through the adhesive barrier;
to form a strong enough union which provides a uniform distribution of stresses over the entire applied area;
to adhere quickly to moist tissues at body temperature;
to be easily sterilizable, and
to be economically satisfactory.

In the use of adhesives for biomedical applications, there are also other factors apart from the immediate bonding. Thus for instance, chemical interference by moisture (blood), or fat (lipids) can change the surface properties of adherents and will affect the wettability. Also, the changing nature of the substrate may give rise to different initial exothermic chemical reactions during the formation of the adhesive joint.

In the past few decades there have been several studies on the bonding strength between bone and different adhesives such as epoxy resins, polyurethanes, polyacrylates, polymethacrylates and composite resins used in dentistry. A brief review of some specific prior references is hereafter presented.

Polyurethanes were extensively investigated about thirty years ago as adhesive reagents for bones. However, it was concluded that their use was not satisfactory for this application [G. Meyer et al, Biomat.Med.-Dev.Art Org. 7(1), 55-71, 1979].

Alkyl-2-cyanoacrylates were also suggested and found to polymerize quite rapidly when applied to dry tissue surfaces. However, due to the exothermic polymerization and toxic degradation products, necrosis of surrounding tissue has been observed. Furthermore, it was found that these adhesives formed an impenetrable barrier between adjacent tissues thus interrupting the natural healing processes until biodegradation was accomplished.

In a very recent paper (J. Kilpikari et al, J. of Biomedical Materials Research, 20, 1095-1102, 1986) there are reported results on the bonding strength of alkyl-2-cyanoacrylates to bone in vitro. Although initially, the strength was quite high, it decreased after three weeks. According to the U.K. Patent No. 1,489,163 adhesive compositions for soft body tissues are suggested, being prepared from an aromatic diisocyanate, a macrodiisocyanate of a particular formula and 2,4,6-tris-(dimethylaminomethyl)phenol. Such adhesives are mentioned that were tested for effectiveness in the gluing of soft tissues of animal, in plastic repair of aponeurosis of the anterior abdominal wall and for reinforcing a cerebral aneurysm. A highly elastic porous polymeric film was formed on the vessel surface.

According to the European patent application No. 244,688 there are provided adhesive formulations for biomedical applications comprising: (a) a polyphenolic protein component of a specific decapeptide formula; (b) a cross-linking agent for the decapeptide; (c) a surfactant functioning as a spreading agent, and (d) a filler compatible with the intended use. Preferred surfactants which are suggested are sodium dodecylsulfate and sodium-dodecylsulfonate. The ratios between the above components depend according to the specific use intended for said compositions, e.g. biomedical adhesive in orthopedic repairs, ophthalmic adhesive for healing perforations, attachement of lenses or corneal components parts, dental adhesive to hold crown in place, medical adhesive for attachement of soft tissues, etc.

According to U.S. Pat. No. 4,740,534 surgical flexible adhesive with improved elasticity are obtained by a reaction betwen at least one NCO-terminated hydrophilic urethane, derived from a polyisocyanate and a polyol, and at least one unsaturated cyanoacrylate compound containing a cyano group attached to a carbon atom constituting the polymerizable double bond. The results submitted in the patent show that very fast curing times are achieved, but nothing is mentioned therein regarding the strength of the bonding which was obtained. The adhesives are supposed to be particularly useful for tisues such as blood vessels, heart, lung, esophagus, stomach, skin and the like.

The above brief review illustrates the long felt want for obtaining biomedical adhesive compositions for soft and calcified tissues which could be able to replace the conventional metal osteosynthesis devices.

It is an object of the present invention to provide new biomedical adhesive compositions for calcified tissues. It is another object of the present invention to provide new biomedical adhesive compositions for calcified tissues which are biocompatible and biodegradable. It is a further object of the present invention to provide new biomedical adhesive compositions which provide adequate tensile strengths during the time of healing of the treated fracture. It is yet another object of the present invention to provide biomedical adhesive compositions which are not interfering with the natural healing process of the injured bone.

BRIEF DESCRIPTION OF THE INVENTION

The invention relates to non-elastomeric biomedical adhesive compositions for calcified tissues consisting of a network to be obtained by the reaction of a polyisocyanate having at least two isocyanates groups, in an amount which ranges between 20% to 80% by weight of the total amount of reactants with at least one polyol which possesses surface wetting properties in amount of between 10% to 80% by weight of the total amount of reactants with the participation of compounds containing calcium and phosphorus, optional in the presence of a catalyst. The adhesive compositions according to the present invention were found to be stable in a phosphate buffered solution at 37° C. and susceptible to enzymatic degradation. It was found that the network formed in the reaction between the constituents does occur even without a promoter for crosslinking.

The temperature required for the reaction is the ambient one or slightly above, but it does not surpass a maximum temperature of above 42° C. Since the reaction is slightly exothermic, no external heating is generally required. An important property of the adhesive compositions, according to the present invention, is the relatively fast strength imparted in gluing of bone tissues which is not affected by the presence of blood or moisture from a biological fluid. As known, the living tissue is very complex, being characterized by a mosaic structure composed of alternating hydrophilic sections. Consequently, hydrophilic and hydrophobic interactions have to be considered in selecting a proper composition. The mechanism which governs the gluing operation might be explained by the interaction of the adhesive at the hydrophilic sections of the tissue, when it does displace moisture from these sections creating a strong adhesion joint. The healing process does occur in the living tissue after gluing. It seems that the structure of the adhesive joint resulting from the use of the compositions according to the present invention, does not prevent this healing process and even contribute to this process under optimum conditions, due to fixation of the bone fragments and their proper location as found from some in-vivo experiments.

The reagents possessing a diisocyanate ot triisocyanate groups useful for the present invention may be selected from a large number of aliphatic, alicyclic and aromatic compounds and some illustrative examples are as follows: 4,4',4''-triphenylmethane triisocyanate, tolylene 2,4-diisocyanate, tolylene 2,6-diisocyanate or any mixture thereof; 1,3-phenylene diisocyanate, 1,4-phenylene diisocyanate, 1,12-diisocyanatododecane, 1,6-diisocyanatohexane, isophorone diisocyanate, each of them either alone or any combinations thereof, etc.

The polyol constituent may be selected from broad classes of compounds which comprise polyalkylene ether glycols, polyester glycols, preferably being those containing between 10 and 80 carbon atoms and most preferably between 25 and 55. Some illustrative examples of useful polyol constituents are as follows: sorbitan monolaurate, sorbitan monostearate, polyoxyethylene (20) sorbitan monopalmitate, polyoxyethylene (20) sorbitan monooleate, sorbitan monopalmitate, octyl gallate, hexyl resorcinol, glycol monostearate, lauryl gallate, sorbitan monolaureate, polyoxyethylene (20) sorbitan monolaureate, polyoxyethylene (20) sorbitan monostearate, acting by themselves or by any mixture thereof. It was found that the wetting properties of the polyol are absolutely required in order to obtain the adhesive compositions according to the present invention. When a polyol which does not possess these properties was used, the adhesive property was very poor (see comparative Example 12).

As additional polyols which may be added to participate in the reaction, the following are mentioned: glycerol, ethylene glycol, polyethylene glycol, polypropylene glycol, polytetrahydrofuran, polycaprolactone diol, polycaprolactone triol, etc.

Among the constituents which were found to participate in the reaction for obtaining the adhesive compositions according to the present invention, there are those compounds containing calcium and phosphorus. In an experiment carried out without the incorporation of these compounds, the strength of the joint resulted with the adhesive composition was found to be very weak (see comparative Example 11). It seems that these compounds contribute to a large extent to the network resulted in the adhesion of the calcified tissue and to the joint strength. Some illustrative examples of a few compounds found to be useful by their presence are as follows: tricalcium phosphate, hydroxyapatite in its pure form or containing traces of magnesium or sodium, esters of calcium salts of phosphoric acids such as: calcium salt of phosphorglyceric acid, glucose-6-calcium salt of phosphoric acid, glucose-1-calcium salt of phosphoric acid and calcium salt of D(-)3 phosphoglyceric acid.

The catalyst useful for the reaction may be selected from the broad classes of compounds, as known in the art for this purpose. Some typical examples are: sodium trichlorophenate, sodium tetrachlorophenate, sodium pentachlorophenate, ferric 2-ethylhexanoate, ferric acetylacetonate, dibutyltin di-2 ethylhexanoate, stannous 2-ethylhexanoate, cobalt 2-ethyl-hexanoate, etc.

The adhesive compositions according to the present invention may contain, if necessary, various additives provided that they are compatible with human tissues, such as: fillers selected from carbon black, metal oxides, silicates, various ceramic powders, acrylic and methacrylic resin powders; stabilizers such as diphenyl-p-phenylene diamine, trimethyldihydroquinone, plasticizers, etc. All these agents are not participating in the reaction which does produce the network of the adhesive composition.

One of the characteristics of the adhesive compositions is the high porous structure with open pores. The existence of the high porous structure is of great importance in the bone healing process. One of the advantages of the glue compositions is the fact that the setting of the adhesive takes place after a short period of time, which generally is in the order of a few minutes.

The adhesive compositions according to the present invention were found to produce fast bonding of the calcified tissues, joint strength of at least 0.2 N/sq.mm and generally joint strength of above 0.5 N/sq.mm being achieved Moreover, the bone joints formed with the adhesive compositions, immersed in phosphate buffered saline solution at 37° C. were found to be stable after prolonged periods of time. It was found that the surface wetness of bones on which the adhesive composition was applied did not weaken the tensile strength of this joint.

It was found that the adhesive compositions are biodegradable allowing growth of the new tissue soon after the surgery, fact which indicates the beginning of the healing process. No adverse reactions were found in tissues neither at the operation site nor in internal organs (lymphomatic glands, spleen, lungs, liver and kidney) after a period of seven months. This indicates biocompatibility of the adhesive and of its degradation products. Tests carried out in-vivo, on the tibia of a dog, showed that the presence of the adhesive in the animal body caused neither inflammation nor major irritation of the tissue around the broken tibia. Also, no evolution of fever was detected in said dog. No adverse reactions were discovered in the animal after periods of up to six months. The X-ray of a bone fracture taken two weeks after the gluing, shows that the adhesive prevented any dislocation of the fracture fragment. The presence of ingrowth of new connective tissue in the location of the adhesive, as shown by microscopic tissue examination, after decalcification of the operated bone, proved the beginning of healing process.

Among the main advantages of the bioadhesive compositions according to the present invention, the following can be mentioned:

The constituents of the compositions possess adequate shelf life at ambient conditions.

They can be produced easily in large scale.

They are able to be sterilized by recognized methods.

They can be packaged in a form allowing antiseptic handling and transfer.

Their initial setting time is reasonable without affecting the normal time of surgery.

The invention will be herinafter illustrated by a number of Examples, being understood that no limitation should be implied by these Examples which are presented only for a better understanding of the invention.

It should be pointed out that Examples 10, 11 and 12 do not illustrate the present invention being presented for comparison purposes only.

In the Examples the concentrations are given in weight percentage unless otherwise stated.

EXAMPLE 1

An amount of 9.5 meq. of Ca-salt of phosphorglyceric acid was added to 4.8 meq. of polyoxyethy sorbitan monolaurate (Tween 20, Trade Mark produced by Atlas Chem) while stirring. After a thorough stirring, an amount of 46 meq. of tolylene diisocyanate (TDI) was added in portions. The mixture was stirred, followed by the introduction of 0.1 g of 2-ethyl-hexanoic acid tin salt as catalyst. The mixture was stirred and the adhesive, still liquid, was spread on the bone specimen by the use of a glass rod and held under the pressure of about 300 g for about 3 min. The strength of the bone joint, after immersion in a phosphate buffered saline solution at 37° C. for 4 days, was 0.31 N/sq.mm.

EXAMPLE 2

The experiment as in Example 1 was repeated using the same reagents and the same amounts, but without adding the catalyst.

The resulted adhesive composition was spread on the bone specimen by the use of a glass rod and held under the pressure of about 300 g for 15 minutes. The strength of the bone joint, after immersion in a phosphate buffered saline solution at 37° C. for 16 days was 0.94 N/sq.mm.

EXAMPLE 3

The experiment as in Example 1 was repeated using the same reagents and catalyst and the same amounts, except the amount of TDI which in this experiment was 13.7 meq. instead of 46 meq.

The resulted adhesive composition was spread on the bone specimen by the use of a glass rod and held under the pressure of about 300 g for about 5 minutes. The strength of the bone joint, after immersion in a phosphate buffered saline solution at 37° C. for 16 days was 0.27 N/sq.mm.

EXAMPLE 4

An amount of 9.5 meq. of glycerophosphate calcium salt was added to 4.6 meq. of polyoxyethylenesorbitan monooleate (Tween 80, Trade Mark produced by Atlas Chem.) while stirring. After about 24 hours of stirring, 46 meq of TDI was added in portions. After the last addition of the TDI, the mixture was thoroughly stirred, followed by the introduction of 0.1 g of 2-ethyl-hexanoic acid tin salt. The mixture was again stirred and the adhesive, still liquid, was spread on the bone specimens by the use of a glass rod and held under a pressure of about 300 g for 5 minutes. The strength of the bone joint, after immersion of one day in a phosphate buffered saline solution at 37° C. was 0.31 N./sq.mm.

EXAMPLE 5

The experiment as in Example 4 was repeated using the same reagents and amounts except the following:

TDI was replaced by 32 meq. of 4,4'-diphenylmethyl-diisocyanate (MDI) and 4.6 meq. of Tween 80 was replaced by 4.9 meq. of Tween 20 (Trade Mark produced by Atlas Chem). The reaction conditions and the testing of the bone joint were the same as in Example 4, the strength of the bone joint was 0.39 N/sq.mm.

EXAMPLE 6

The experiment as in Example 1 was repeated using the same reagents and amounts, except that 2.0 g of hydroxyapatite was used instead of 9.5 meq. of the calcium salt of phosphorglyceric acid. The reaction conditions were the same as in Example 1.

The adhesive composition was spread on the bone specimens by the use of a glass rod and held under a pressure of about 300 g for about 5 minutes. The strength of the bone joint after immersion of 2 days in a phosphate buffered saline solution at 37° C. was 0.43 N/sq.mm.

EXAMPLE 7

The experience as in Example 1 was repeated using the same reagents except that 4.7 meq. of polyoxyethylenesorbitan monopalmitate (Tween 40 Trade Mark produced by Atlas Chem) were used instead of the Tween 20. The same amounts of reagents were used, except that only 0.02 g of the catalyst were added.

The adhesive composition was spread on the bone specimen, and tested as described in Example 6. The strength of the bone joint was 0.9 N/sq.mm.

EXAMPLE 8

An amount of 9.5 meq of calcium salt of phosphorglyceric acid was added under stirring to a mixture of 3.5 meq of Tween 40 and 16.3 meq of glycerine. After 24 hours of stirring, 38 meq of TDI were added in a single portion. No catalyst was added in this experiment. The mixture was stirred for less than 1 minute and the adhesive, still liquid, was spread on the bone specimens by the use of a glass rod and held under a pressure of about 300 g for 5 minutes. The strength of the bone joint after immersion of 2 days in a phosphate buffered saline solution at 37° C. was 0.6 N/sq.mm.

EXAMPLE 9 (In-Vivo Adhesion)

The surgery was performed on a dog (18 kg) anesthetized with Nembutal (30 mg/kg). Preparation of the operative area included shaving and washing the skin with Betadine. A 5 cm incision of the cutis was made in the mid third of the tibia, followed by opening of the deep fascia and separation between the subperiosteum and the bone.

From the front of the tibia a cortical slice, with a square base of 0.7 cm×0.7 cm, was removed.

A small amount of the glue, as obtained in Example 1, was spread on the tissue around the exposed bone, following a process of the site cleaning, and the bond fragment was replaced in its original position. The dermis was closed and the leg was bandaged and placed in a plaster of Paris cast.

Six weeks later the surgical procedure was repeated on the dog and the tibia was exposed. It was found that the tissues close to the adhesion site were not inflamed or infected. The fragment which was glued on six weeks before was still in place. Attempts to remove the fragment by forceps did not succeed.

EXAMPLE 10 (Comparative)

The experiment as in Example 1 was repeated but instead of the sorbitan an amount of 3.1 meq. of polyethylene glycol tert-octylphenyl ether (Triton 100, Trade Mark, produced by Rohm & Haas) was utilized.

The adhesive composition was spread on the bone fracture, in the same manner as in Example 1. No strength at all for the joint could be measured, after immersion in a phosphate buffered saline solution for 24 hours and the bone fracture was noticed.

EXAMPLE 11 (Comparative)

The experiment as in Example 1 was repeated using the same reagents and amounts, except the calcium salt of phosphorglyceric acid which was omitted.

The adhesive composition was spread on the bone fracture in the same manner as in Example 1. No strength at all for the joint could be measured, after immersion in a buffer solution for 48 hours and the bone fracture was noticed.

EXAMPLE 12 (Comparative)

The experiment as in Example 1 was repeated, but instead of polyoxyethylene sorbitan monolaureate (Tween 20), an equivalent amount of dextrin (i.e a polyol which does not possess wetting agent properties) was used.

It was found that this composition did not possess an adhesive property even after prolonged setting time.

EXAMPLES 13-23

A number of experiments were carried out using the general procedure and reaction conditions as described in the above Examples, using various polyols, polyisocyanates and compounds containing calcium and phosphorus.

The data of these experiments and the strength of the bone joint after immersion in a phosphate buffered saline solution at 37° C. are sumarized in the following Table.

| Ex. No. | Polyol used | Isocyanate used | Ca-P compound. | Strength N/ sq. mm | after days |
|---|---|---|---|---|---|
| 13[1] | 4.8 meq A | 63.2 meq a | 16 meq L | 0.52 | 2 |
| 14 | 7.6 meq B | 46 meq b | 4.7 meq L | 0.43 | 3 |
| 15[2] | 5.25 meq C | 27.6 meq c | 0.5 g N | 0.24 | 3 |
| 16 | 6.15 meq D | 16 meq c | 2.3 meq L | 0.39 | 1 |
| 17 | 7.05 meq E | 9.0 meq e | 0.5 g P | 0.38 | 5 |
| 18 | 12.55 meq F | 23 meq f | 0.5 g N | 0.4 | 2 |

-continued

| Ex. No. | Polyol used | Isocyanate used | Ca-P compound. | Strength N/ sq. mm | after days |
|---|---|---|---|---|---|
| 19 | 17 meq G | 9.0 meq e | 9.5 meq L | 0.7 | 2 |
| 20 | 4.9 meq H | 23 meq c | 3.1 meq L | 0.32 | 3 |
| 21 | 4.6 meq K | 11.5 meq b | 0.5 g N | 0.34 | 5 |
| 22 | 4.8 meq A | 16.6 meq h | 9.5 meq L | 0.37 | 1 |
| 23 | 4.8 meq A | 27.6 meq b | 4.1 meq R | 0.46 | 3 |

[1]the reaction mixture was heated at 40° C.
[2]an amount of 0.05 g of 2-ethyl-hexanoic acid as catalyst was added and the polyisocyanate was added in two equal portions.
In the above Table the symbols for the reagents used in the various experiments are as follows:
A = polyoxyethylene sorbitan monolaureate (Tween 20)
a = hexamethylene diisocyanate.
L = Ca-salt of phosphorglyceric acid.
B = 2.8 meq of glycerol monostearate + 4.8 meq Tween 20.
b = 46 meq of tolylene diisocyanate (TDI, commercial mixture of isomers) added in two equal portions.
C = 3.4 meq of Tween 20 + 1.85 meq of polycaprolactone diol.
c = 27.6 meq of TDI added in two equal portions.
N = hydroxyapatite.
D = 1.15 meq of polycaprolactone diol + 5 meq of 4-hexyl resorcinol.
E = 5.2 meq of octyl gallate + 8.4 meq of polycaprolactone diol.
e = isophorone diisocyanate.
P = tricalcium phosphate.
F = 3.75 meq of poly-tetrahydrofuran + 8.8 meq of lauryl gallate.
f = 2,4 TDI (the pure isomers).
G = sorbitan monolaureate.
H = 3.1 meq Tween 20 + 1.8 meq sorbitan monooleate.
K = polyoxyethylene sorbitan monostearate
h = 4,4'4''-triphenylmethane triisocyanate (20% in a methylene chloride solution)
R = calcium salt of D(−3)-phosphoglyceric acid.

We claim:

1. A composition consisting of a network to be obtained by the reaction of a polyisocyanate having at least two isocyanate groups, in an amount which ranges between 20% to 80% by weight of the total amount of reactants with at least one polyol which possesses surface wetting properties in an amount of between 10% to 80% by weight of the total amount of reagents, with the participation of compounds containing calcium and phosphorus, said polyisocyanate being selected from the group consisting of aliphatic, alicyclic and aromatic polyisocyanates, said polyol being selected from the group consisting of polyalkylene ether and glycols containing between 25 and 55 carbon atoms, said compounds containing calcium and phosphorus being present in an amount sufficient to permit said adhesive composition to produce bonding of calcified tissues with a joint strength of at least 0.2 N/sq. mm., said composition being a non-elastomeric biomedical adhesive composition which is degradable by physiological enzymes and which is biocompatible.

2. The non-elastomeric biomedical adhesive composition according to claim 1, wherein said network is obtained in the presence of a catalyst.

3. The non-elastomeric biomedical adhesive composition according to claim 1, wherein said polyisocyanate is: tolylene 2,4-diisocyanate, tolylene 2,6-diisocyanate, 1,3-phenylene diisocyanate, 1,4-phenylene diisocyanate, isophorone diisocyanate, hexamethylene diisocyanate, 1,12-diisocyanatododecane, 1,6-diisocyanatohexane, 4,4',4''-triphenylmethane triisocyanate, mixtures thereof or combinations with another polyisocyanate.

4. The non-elastomeric biomedical adhesive composition according to claim 1, wherein said polyol is polyester glycol containing between 25 and 55 carbon atoms.

5. The non-elastomeric biomedical adhesive composition according to claim 1, wherein said polyol is: sorbitan monolaurate, sorbitan monostearate, polyoxyethylene (20) sorbitan monopalmitate, polyoxyethylene (20)

sorbitan monooleate, sorbitan mono-9-octo-decenoate, lauryl gallate or any mixture thereof.

6. The non-elastomeric biomedical adhesive composition according to claim 1, wherein an additional polyol may be incorporated being selected from the group consisting of: glycerol, ethylene glycol, polyethylene glycol, polypropylene glycol, poly-tetrahydrofuran, polycaprolactone diol, glycerol monostearate and polycaprolactone triol.

7. The non-elastomeric biomedical adhesive composition according to claim 1, wherein said compounds of calcium and phosphorus, are selected from tricalcium phosphate, hydroxyapatite, calcium salt of phosphorglyceric acid, glucose-6-calcium salt of phosphoric acid and glucose-1-calcium salt of phosphoric acid.

8. The non-elastomeric biomedical adhesive composition according to claim 2, wherein the optional catalyst to be used is selected from: sodium trichlorophenate, sodium tetrachlorophenate, sodium pentachlorophenate, ferric 2-ethylhexanoate, ferric acetylacetonate, dibutyltin-di-2-ethylhexanoate, stannous- 2-ethylhexanoate and cobalt 2-ethylhexanoate.

9. The non-elastomeric biomedical adhesive composition according to claim 1, wherein an inert filler is incorpoted.

10. The non-elastomeric biomedical adhesive composition according to claim 9, wherein said inert filler is selected from carbon black, metal oxides, stabilizers, ceramic powders, acrylic and methacrylic resin powders, and plasticizers.

* * * * *